United States Patent [19]

Beuvry et al.

[11] Patent Number: 5,824,653
[45] Date of Patent: Oct. 20, 1998

[54] ANTHELMINTIC COMPOSITIONS FOR EQUIDAE

[75] Inventors: Vincent Beuvry, Coogee; Michael Forster, Sydney, both of Australia

[73] Assignee: Virbac S.A., Carros, France

[21] Appl. No.: 562,932

[22] Filed: Nov. 27, 1995

[30] Foreign Application Priority Data

Nov. 28, 1994 [AU] Australia .................. PM9699

[51] Int. Cl.⁶ .................. A61K 30/70; A61K 31/335
[52] U.S. Cl. .................. 514/30; 514/450
[58] Field of Search .................. 514/30, 450; 536/7.1

[56] References Cited

U.S. PATENT DOCUMENTS 4,624,945  11/1986  Eckenhoff et al. .................. 514/30

FOREIGN PATENT DOCUMENTS 3619030   10/1987  Germany .
84 2571    4/1984  South Africa .
WO 95/05181 2/1995 WIPO .

*Primary Examiner*—Elli Peselev
*Attorney, Agent, or Firm*—Oblon, Spivak, McClelland, Maier & Neustadt, P.C.

[57] ABSTRACT

The Invention relates to an anthelmintic composition for oral use comprising an effective amount of praziquantel and an effective amount of at least one anthelmintic agent selected from avermectins, milbemycins or derivatives thereof and to a method for controlling and treating infestations by cestodes and nematodes in equine animals comprising orally administering such a composition to said animals.

11 Claims, No Drawings

ANTHELMINTIC COMPOSITIONS FOR EQUIDAE

The present invention relates to a composition for the control and the treatment of parasitic infestations in Equidae and, in particular, for simultaneous control and treatment of infestations by roundworms and tapeworms in such animals.

Avermectins and milbemycins are currently used in the treatment and control of roundworms and bots in horses and ponies. However, these compounds are known to be inactive against tapeworms. The widespread use of the anthelmintic ivermectin has recently been linked to a rise in the prevalence of the equine tapeworm *Anoplocephala perfoliata*.

*Anoplocephala perfoliata* is found mainly in the caecum but tends also to cluster in the ileum near the ileocecal valve where it is associated with ulceration and reactive inflammation of the ileal wall. This clustering results in ulceration of the mucous membrane and inflammation with thickening and induration of the deeper layers of the intestinal wall. These pathological changes probably account for some cases of persistent diarrhoea and may predispose to intussusception of the ileum into the caecum or rupture of the bowel wall in the vicinity of the ileocecal valve.

It is therefore highly desirable to have a composition which has activity against both cestode and nematode infestations in Equidae and more particularly in horses.

It is accordingly an object of the present invention to provide a novel veterinary composition adapted to control both cestodes and nematodes in equine animals.

According to the invention, there is provided an anthelmintic composition for oral use comprising an effective amount of praziquantel and an effective amount of at least one anthelmintic agent selected from avermectins or milbemycins or derivatives thereof.

Indeed, trials have shown that, when praziquantel is orally administered to horses in combination with an avermectin or a milbemycin or a derivative thereof, a surprising increase of the anthelmintic spectrum is obtained due to the administration in combination. Furthermore a synergistic effect is observed to the extend that when in combination with avermectins or milbemycins the required dosage rate for praziquantel in equine animals is between 0.5 and 2.0 mg per kg of animal body weight. This synergistic activity is even higher with a paste formula.

Anthelmintic formulations containing praziquantel together with another anthelmintic such as for example levamisole, albendazole, oxfendazole, moxidectin, ivermetin, have been disclosed in the British Patent Application 2 252 730 of Ancare Distributors Limited. However, the various associations disclosed in this Patent Application are not synergistic and only increase the anthelmintic spectrum in sheep. According to Ancare Distributors Limited, the recommended dose rate of praziquantel in such associations is between 2.0 and 7.5 mg per kg of animal body weight.

According to the present invention, it has been discovered that the association between praziquantel and an avermectin or a milbemycin or a derivative thereof shows a surprising synergy in the treatment of horse tapeworms. It allowed the use of praziquantel against *Anoplocephala perfoliata* in Equidae at a dose rate between 0.5 and 2.0 mg per kg of animal body weight. These dosages are significantly lower than in the already described formulations.

Kitano in the European Patent Application 0 059 074 discloses associations of macrolide anthelmintic agents (avermectins) and a variety of several anthelmintic agents like benzimidazole, salicylamide and isoquinoline compounds with enhanced anthelmintic activity. However, Kitano studies on cestodes did not show any evident synergy of any association on *Anoplocephala perfoliata*.

According to the present invention, the activity of praziquantel against *Anoplocephala perfoliata* is increased in association with an avermectin or a milbemycin compound or a derivative thereof.

Moreover, the association exhibits higher synergistic activity as a paste formula which allowed a better biodisponibility of praziquantel in horses.

Praziquantel (2(cyclohexylcarbonyl)-1,2,3,6,7,11b-hexahydro-4H-pyrazino[2,1-a]isoquinolin-4-one) is a relatively insoluble material in water and consequently the applicant has devised formulations for administration of the compound subject of this invention in the form of paste, drench, tablet or pellet.

Examples of formulations in accordance with the present invention will be described hereafter without limiting the generality of the invention as above described.

The range of active percentages of a typical formula in accordance with this invention could be as indicated thereafter:

| | |
|---|---|
| Praziquantel | 0.1–30% w/v |
| and | |
| Ivermectin | 0.05–5% w/v |
| or | |
| Abamectin | 0.05–5% w/v |
| or | |
| Moxidectin | 0.05–5% w/v |
| or | |
| Doramectin | 0.05–5% w/v | and one or more of the following ingredients to enhance stability and/or other characteristics of the composition: surfactants, preservatives, viscosity agents, stabilisers, flavours and colours.

Ivermectin is a semisynthetic derivative of avermectins. Ivermectin contains at least 80% of 22,23-dihydroavermectin B1a and less than 20% of 22,23-dihydroavermectin B1b. Ivermectin is disclosed in Australian Patent 519569.

Abamectin or avermectin B1 contains at least 80% of avermectin B1a and not more than 20% of avermectin B1b. Abamectin is disclosed in Australian Patent 513641.

Moxidectin [spiro (11,5-methano-2Hm13G, 17H-furo(4,3,2-pg) (2,6) benzodioxacyclo octadectin-13,2'-(2H) pyran-7-one,20,20b-dihydroxy-6'(1,3-dimethyl-T-butenyl)=4'-(methoxymino)-3',4',5',6,6',7,10,11,14,15,17a,20,20a, 20b-tetradecahydro-5'6,8,19-teramethyl-(6R-(2aZ,4E,5'S*, 6R*(E),8E,11R*,13S*,15R*,17aR*,20R*,20bS*)] is a new broad spectrum endectocide.

Doramectin (25-cyclohexyl-5-O-demethyl-25-de-1 (methylpropyl)avermectin A1a is an avermectin.

According to the invention, when praziquantel is orally administered in combination with an avermectin, a milbemycin or a derivative thereof, the dosage rate of praziquantel required for efficiently treating equine animals against nematodes and more particularly against *Anoplocephala perfoliata* is between 0.5 and 2.0 mg per kg of animal body weight. However, it has been observed that praziquantel may be administered in higher dosage rates without adverse effects and in this regard dosage rates of up to 7.5 mg per kg of body weight have been tested.

EXAMPLE 1

ABAMECTIN-PRAZIQUANTEL PASTE FOR HORSES

| | |
|---|---|
| ABAMECTIN (AVERMECTIN B1) | 0,4 g |
| PRAZIQUANTEL | 50 g |
| DIETHYLENE GLYCOL PALMITO STEARATE | 80 g |
| SODIUM METABISULFITE | |
| SORBITOL SOLUTION (NON-CRYSTALLISING) | 120 g |
| GLYCEROL FORMAL | 60 ml |
| POLYETHYLENE GLYCOL 400 | 60 ml |
| METHYL HYDROXYBENZOATE | 0,5 g |
| PROPYL HYDROXYBENZOATE | 0,05 g |
| BENZYL ALCOHOL | 10 g |
| OAT MEAL FLOUR | 300 g |
| PURIFIED WATER | q.s. to 1 liter |

The manufacture of the formulations of Example 1 is in accordance with the following procedures:

1. Heat 400 ml of purified water in a separate container to 80 degrees–85 degrees Celsius.

2. While mixing, add and dissolve methyl hydroxybenzoate and propyl hydroxybenzoate. Continue mixing until all has dissolved.

3. While mixing, add Sorbitol solution. Maintain the temperature at 70 degrees Celsius.

4. In a separate container, add glycerol formal, polyethylene glycol 400, benzyl alcohol. Start mixing while warming to 35 degrees–40 degrees Celsius.

5. While mixing, add abamectin. Continue mixing until all has dissolved. Maintain temperature at 35 degrees–40 degrees Celsius.

6. In the ointment tank, add half of the Oat Flour, the praziquantel, then start mixing. Continue mixing for 5–10 minutes until a homogeneous blended powder is formed. The add the rest of the Oat Flour and continue mixing.

7. While mixing the powders, add the solution from step 5 in a thin stream. When all is added, continue mixing until an homogenous mass is formed.

8. Melt diethylene glycol palmitostearate in a separate container. While mixing the solution form step 3, add the melted wax and continue mixing to form an homogeneous emulsion. Stop heating and mix to cool to 40 degrees–45 degrees Celsius.

9. Add and dissolve sodium metabisulphite in the emulsion.

10. While mixing the mass from step 7, add gradually and in a thin stream the emulsion from step 9. The emulsion when added should be at 40 degrees–45 degrees Celsius.

11. When all is added, continue mixing for 10–15 minutes.

12. Complete the batch to volume with purified water while mixing. Continue mixing for 30 minutes. Stop when the batch temperature is not higher than 30 degrees Celsius. Check on Specific Gravity (1.05–1.09).

13. Homogenise the batch.

14. Pack in syringes.

Combinations with other avermectins or milbemycin type compounds can be formulated in a manner similar to that of Example 1.

EXAMPLE 2

ABAMECTIN-PRAZIQUANTEL PASTE FOR HORSES

We use the ingredients, dosages and manufacturing process for Example 1 except for abamectin which is used in an amount of 2 g instead of 0.4 g.

EXAMPLE 3

ABAMECTIN-PRAZIQUANTEL PASTE FOR HORSES

We use the ingredients, dosages and manufacturing process of Example 1 except for abamectin which is used in an amount of 4 g instead of 0.4 g.

EXAMPLE 4

ABAMECTIN-PRAZIQUANTEL PASTE FOR HORSES

We use the ingredients, dosages and manufacturing process of Example 1 except for abamectin which is used in an amount of 8 g instead of 0.4 g.

EXAMPLE 5

ABAMECTIN-PRAZIQUANTEL PASTE FOR HORSES

We use the ingredients, dosages and manufacturing process of Example 1 except for abamectin which is used in an amount of 20 g instead of 0.4 g.

EXAMPLE 6

IVERMECTIN-PRAZIQUANTEL ORAL DRENCH FOR HORSES

| | |
|---|---|
| IVERMECTIN | 2 g |
| PRAZIQUANTEL | 50 g |
| GLYCEROL FORMAL | 250 ml |
| TWEEN 80 | 120 g |
| BENZYL ALCOHOL | 30 g |
| XANTHAM GUM | 1 g |
| PURIFIED WATER | q.s. to 1 liter |

Other Avermectins such as abamectin or doramectin or milbemycins such as moxidectin may be used in place of ivermectin.

EXAMPLE 7

IVERMECTIN-PRAZIQUANTEL ORAL DRENCH FOR HORSES

We use the ingredients, dosages and manufacturing process of Example 6 except for ivermectin which is used in an amount of 4 g instead of 2 g.

EXAMPLE 8

IVERMECTIN-PRAZIQUANTEL ORAL DRENCH FOR HORSES

We use the ingredients, dosages and manufacturing process of Example 6 except for ivermectin which is used in an amount of 8 g instead of 2 g.

EXAMPLE 9

ABAMECTIN-PRAZIQUANTEL TABLET FOR HORSES

1 Tablet/200 kg body weight

|  | Per Tablet |
| --- | --- |
| ABAMECTIN | 40 mg |
| PRAZIQUANTEL | 200 mg |
| SODIUM STARCH GLYCOLLATE | 12 g |
| HYDROXY PROPYL CELLULOSE | 4 mg |
| LACTOSE | 178 mg |
| COLLOIDAL SILICON DIOXIDE | 4 mg |
| MAGNESIUM STEARATE | 2 mg |

Other avermectins or milbemycins can be used instead of abamectin.

TRIALS

Trials of formulations in accordance with the present invention have been conducted in Australia.

The method of evaluating the activity of the formulation was a modified critical test (Lyons et al., 1986) which involved killing the horses 24 hours after treatment.

Efficacy is the number of worms count dead and removed versus the number of worms count alive and not removed (scolex attached for *Anaplocephala perfoliata*).

EXAMPLE 10

TRIAL 1

A trial involving abamectin paste (1 ml per 20 kg of body weight equivalent to 0.2 mg of Abamectin per kg B.W.), praziquantel paste (0.1 to 5 mg of Praziquantel per kg of body weight), and formulations in accordance with examples 1,2,3,4 and 5.

Eleven groups of ten horses per group were involved in the study. Area of origin of the horses was well known for having internal parasitism problem and specifically tapeworms (*Anaplocephala perfoliata*) infestation.

A high level of efficacy was demonstrated by the combination formula of Examples 2, 3, 4 and 5 against roundworms, anthropod parasites and tapeworms.

Synergistic activity of praziquantel and abamectin shows 100% removal of *Anoplocephala perfoliata* with 0.2 mg of abamectin per kg B.W. and 1 mg of praziquantel per kg B.W.

EFFICACY OF THE FORMULATION OF EXAMPLES 1, 2, 3, 4 and 5 AGAINST NEMATODES, ARTHROPOD PARASITES AND CESTODES IN HORSES IN A CRITICAL TRIAL

| Anthelmintic | Dosage mg/kg | % Efficacy Strongylidase | % Efficacy Gasterophilus spp. | % Efficacy *Parascaris equorum* | % Efficacy *Anoplocephala perfoliata* |
| --- | --- | --- | --- | --- | --- |
| Abamectin | 0.2 | 100 | 100 | 100 | 0 |
| Praziquantel | 0.1 | 0 | 0 | 0 | 0 |
| Praziquantel | 0.5 | 0 | 0 | 0 | 27 |
| Praziquantel | 1 | 0 | 0 | 0 | 51 |
| Praziquantel | 2 | 0 | 0 | 0 | 71 |
| Praziquantel | 5 | 0 | 0 | 0 | 33 |
| Abamectin | 0.2 | 100 | 100 | 100 | |
| Praziquantel | 0.1 | | | | 39 |
| Abamectin | 0.2 | 100 | 100 | 100 | |
| Praziquantel | 0.5 | | | | 89 |
| Abamectin | 0.2 | 100 | 100 | 100 | |
| Praziquantel | 1 | | | | 100 |
| Abamecitin | 0.2 | 100 | 100 | 100 | |
| Praziquantel | 2 | | | | 100 |
| Abamectin | 0.2 | 100 | 100 | 100 | |
| Praziquantel | 5 | | | | 100 |

EXAMPLE 11

TRIAL 2

A trial involving Ivermectin drench (1 ml per 10 kg of body weight equivalent to 0.2 mg of Ivermectin per kg B.W.), praziquantel drench (0.5 to 2 mg of praziquantel per kg of body weight), and formulations in accordance with Examples 6, 7 and 8.

Seven groups of 6 horses per group were involved in the study. Area of origin of the horses was well known for having internal parasitism problem and specifically tapeworms (*Anoplocephala perfoliata*) infestation.

A high level of efficacy was demonstrated by the combination formula of Examples 7 and 8 against roundworms, arthropod parasites and tapeworms.

Synergistic activity of praziquantel and ivermectin shows 100% removal of *Anoplocephala perfoliata* with 0.2 mg of ivermectin per kg B.W. and 2 mg of praziquantel per kg B.W.

EFFICACY OF THE FORMULATION OF
EXAMPLES 6, 7 AND 8 AGAINST
NEMATODES, ARTHROPOD PARASITES AND
CESTODES IN HORSES IN A CRITICAL TRIAL

| Anthelmintic | Dosage mg/kg | % Efficacy Strongylidase | % Efficacy Gasterophilus spp. | % Efficacy Parascaris equorum | % Efficacy Anoplocephala perfoliata |
|---|---|---|---|---|---|
| Ivermectin | 0.2 | 100 | 100 | 100 | 0 |
| Praziquantel | 0.5 | 0 | 0 | 0 | 21 |
| Praziquantel | 1 | 0 | 0 | 0 | 43 |
| Praziquantel | 2 | 0 | 0 | 0 | 59 |
| Ivermectin | 0.2 | 100 | 100 | 100 | |
| Praziquintel | 0.5 | | | | 68 |
| Ivermectin | 0.2 | 100 | 100 | 100 | |
| Praziquantel | 1 | | | | 91 |
| Ivermectin | 0.2 | 100 | 100 | 100 | |
| Praziquantel | 2 | | | | 100 |

We claim:

1. An anthelmintic composition for orally controlling and treating an infestation by *Anoplocephala perfoliata* in equine animals comprising an amount of a combination of praziquantel together with at least one anthelmintic agent selected from the group consisting of avermectins and milbemycins suitable for administering to said equine animals a dose of 0.5 to 2.0 mg of praziquantel and of about 0.2 mg of said anthelmintic agent per kg of animal body weight.

2. An anthelmintic composition according to claim 1, wherein the anthelmintic agent is an anthelmintic agent.

3. An anthelmintic composition according to claim 2, wherein the avermectin is abamectin.

4. An anthelmintic composition according to claim 1, wherein the anthelmintic agent is ivermectin.

5. An anthelmintic composition according to claim 1, wherein the anthelmintic agent is moxidectin.

6. An anthelmintic composition according to claim 1, which is in the form of a paste.

7. A method for controlling and treating an infestation by *Anoplocephala perfoliata* in equine animals, comprising orally administering to said animals, a dose of 0.5 to 2.0 mg of praziquantel per kg of animal body weight in combination with a dose of about 0.2 mg of an anthelmintic agent selected from the group consisting of avermectins and milbemycins per kg of animal body weight.

8. A method according to claim 7, wherein the anthelmintic agent is an avermectin.

9. A method according to claim 8, wherein the anthelmintic agent is abamectin.

10. A method according to claim 7, wherein the anthelmintic agent is ivermectin.

11. A method according to claim 7, wherein the anthelmintic agent is moxidectin.

* * * * *

UNITED STATES PATENT AND TRADEMARK OFFICE
CERTIFICATE OF CORRECTION

PATENT NO. : 5,824,653

DATED : OCTOBER 20, 1998

INVENTOR(S) : VINCENT BEUVRY ET AL.

Page 1 of 4

It is certified that error appears in the above-identified patent and that said Letters Patent is hereby corrected as shown below:

Column 3, line 8, "SODIUM METABISULFITE         "
    should read --SODIUM METABISULFITE      1g--.

Column 5, Example 9, line 12,
"SODIUM STARCH GLYCOLLATE      12 g" should read
--SODIUM STARCH GLYCOLLATE    12mg--.

Column 6, line 4, "anthropod" should read --arthropod".

Column 6, lines 18-39

"

| Anthelmintic | Dosage mg/kg | % Efficacy Strongylidase | % Efficacy Gasterophilus spp | % Efficacy Parascaris equorum | % Efficacy Anoplocephala perfoliata |
|---|---|---|---|---|---|
| Abamectin | 0.2 | 100 | 100 | 100 | 0 |
| Praziquantel | 0.1 | 0 | 0 | 0 | 0 |
| Praziquantel | 0.5 | 0 | 0 | 0 | 27 |
| Praziquantel | 1 | 0 | 0 | 0 | 51 |
| Praziquantel | 2 | 0 | 0 | 0 | 71 |
| Praziquantel | 5 | 0 | 0 | 0 | 33 |
| Abamectin | 0.2 | 100 | 100 | 100 | |
| Praziquantel | 0.1 | | | | 39 |
| Abamectin | 0.2 | 100 | 100 | 100 | |
| Praziquantel | 0.5 | | | | 89 |
| Abamectin | 0.2 | 100 | 100 | 100 | |
| Praziquantel | 1 | | | | 100 |
| Abamectin | 0.2 | 100 | 100 | 100 | |
| Praziquantel | 2 | | | | 100 |
| Abamectin | 0.2 | 100 | 100 | 100 | |
| Praziquantel | 5 | | | | 100 |

"

UNITED STATES PATENT AND TRADEMARK OFFICE
CERTIFICATE OF CORRECTION

PATENT NO. : 5,824,653
DATED : OCTOBER 20, 1998
INVENTOR(S) : VINCENT BEUVRY ET AL.

It is certified that error appears in the above-identified patent and that said Letters Patent is hereby corrected as shown below:

should read

| Anthelmintic | Dosage mg/kg | % Efficacy Strongylidae | % Efficacy Gasterophilus spp. | % Efficacy Parascaris equorum | % Efficacy Anoplocephala perfoliata |
|---|---|---|---|---|---|
| Abamectin | 0.2 | 100 | 100 | 100 | 0 |
| Praziquantel | 0.1 | 0 | 0 | 0 | 0 |
| Praziquantel | 0.5 | 0 | 0 | 0 | 27 |
| Praziquantel | 1 | 0 | 0 | 0 | 58 |
| Praziquantel | 2 | 0 | 0 | 0 | 71 |
| Praziquantel | 5 | 0 | 0 | 0 | 83 |
| Abamectin Praziquantel | 0.2 0.1 | 100 | 100 | 100 | 39 |
| Abamectin Praziquantel | 0.2 0.5 | 100 | 100 | 100 | 89 |
| Abamectin Praziquantel | 0.2 1 | 100 | 100 | 100 | 100 |
| Abamectin Praziquantel | 0.2 2 | 100 | 100 | 100 | 100 |
| Abamectin Praziquantel | 0.2 5 | 100 | 100 | 100 | 100 |

UNITED STATES PATENT AND TRADEMARK OFFICE
CERTIFICATE OF CORRECTION

Page 3 of 4

PATENT NO. : 5,824,653
DATED : OCTOBER 20, 1998
INVENTOR(S) : VINCENT BEUVRY ET AL.

It is certified that error appears in the above-identified patent and that said Letters Patent is hereby corrected as shown below:

Column 7, lines 7-20

"

| Anthelmintic | Dosage mg/kg | % Efficacy Strongylidase | % Efficacy Gasterophilus spp. | % Efficacy Parascaris equorum | % Efficacy Anoplocephala perfoliata |
|---|---|---|---|---|---|
| Ivermectin | 0.2 | 100 | 100 | 100 | 0 |
| Praziquantel | 0.5 | 0 | 0 | 0 | 21 |
| Praziquantel | 1 | 0 | 0 | 0 | 43 |
| Praziquantel | 2 | 0 | 0 | 0 | 59 |
| Ivermectin | 0.2 | 100 | 100 | 100 | |
| Praziquantel | 0.5 | | | | 68 |
| Ivermectin | 0.2 | 100 | 100 | 100 | |
| Praziquantel | 1 | | | | 91 |
| Ivermectin | 0.2 | 100 | 100 | 100 | |
| Praziquantel | 2 | | | | 100 | should read

| Anthelmintic | Dosage mg/kg | % Efficacy Strongylidae | % Efficacy Gasterophilus spp. | % Efficacy Parascaris equorum | % Efficacy Anoplocephala perfoliata |
|---|---|---|---|---|---|
| Ivermectin | 0.2 | 100 | 100 | 100 | 0 |
| Praziquantel | 0.5 | 0 | 0 | 0 | 21 |
| Praziquantel | 1 | 0 | 0 | 0 | 43 |
| Praziquantel | 2 | 0 | 0 | 0 | 59 |
| Ivermectin Praziquantel | 0.2 0.5 | 100 | 100 | 100 | 68 |
| Ivermectin Praziquantel | 0.2 1 | 100 | 100 | 100 | 91 |
| Ivermectin Praziquantel | 0.2 2 | 100 | 100 | 100 | 100 |

"

UNITED STATES PATENT AND TRADEMARK OFFICE
CERTIFICATE OF CORRECTION

PATENT NO. : 5,824,653
DATED : OCTOBER 20, 1998
INVENTOR(S) : VINCENT BEUVRY ET AL.

It is certified that error appears in the above-identified patent and that said Letters Patent is hereby corrected as shown below:

Column 7, line 31, "anthelmintic agent" (2nd Occurrence) should read-- avermectin--.

Signed and Sealed this

Fifth Day of October, 1999

Attest:

Q. TODD DICKINSON

*Attesting Officer*    *Acting Commissioner of Patents and Trademarks*